United States Patent [19]

Imondi et al.

[11] Patent Number: 5,091,175
[45] Date of Patent: Feb. 25, 1992

[54] PHARMACEUTICAL COMPOSITION CONTAINING BILE ACID SEQUESTRANT ENCLOSED IN A SIZE-EXCLUSION MEMBRANE

[75] Inventors: Anthony R. Imondi, Westerville; Larry M. Hagerman, Columbus, both of Ohio

[73] Assignee: Erbamont Inc., Minn.

[21] Appl. No.: 523,163

[22] Filed: May 14, 1990

[51] Int. Cl.$^5$ .............. A61K 9/18; A61K 9/24; A61K 9/16; A61K 31/785

[52] U.S. Cl. ............... 424/486; 424/452; 424/456; 424/457; 424/461; 424/462; 424/460; 424/469; 424/470; 424/473; 424/493; 424/494; 424/495; 424/496; 424/497; 424/501; 424/DIG. 7; 424/78.12; 514/824

[58] Field of Search ........... 424/78, 456, 493–497, 424/501, 486, DIG. 7, 79; 514/824, 962

[56] References Cited

U.S. PATENT DOCUMENTS 3,974,272  8/1976  Polli et al. ............... 424/78
4,362,711  12/1982  Cerami ............... 424/497
4,747,881  5/1988  Shaw et al. ............... 424/498
4,902,501  2/1990  Bandi et al. ............... 424/79

OTHER PUBLICATIONS

Publication titled "Sampling Intestinal Content with a Sequestering Capsule", Mayo Clin Proc, Mar. 1976, vol. 51 by Neville E. Hoffman et al.

*Primary Examiner*—Thurman K. Page
*Assistant Examiner*—E. J. Webman
*Attorney, Agent, or Firm*—Thompson, Hine and Flory

[57] ABSTRACT

A pharmaceutical composition useful for treating hypercholesterolemia comprising a bile acid sequestrant resin such as cholestyramine and cholestipol maintained in a semipermeable water-insoluble material; wherein said semipermeable material enables bile acids from the digest tract to contact and bind to said resin while preventing substances having a higher molecular weight than bile acids from contacting said resin material. A method for treating hypercholesterolemia using the inventive composition is also disclosed.

25 Claims, No Drawings

PHARMACEUTICAL COMPOSITION CONTAINING BILE ACID SEQUESTRANT ENCLOSED IN A SIZE-EXCLUSION MEMBRANE

BACKGROUND OF THE INVENTION

1. Field of the Invention

The present invention relates to a pharmaceutical composition for treating hypercholesterolemia, and more particularly, to a pharmaceutical composition comprising a bile acid sequestrant resin maintained in a membrane to prevent materials having a higher molecular weight than bile acids from binding to the resin and thereby to enhance the efficiency of the resin in binding bile ids 2. Description of the Prior Art Hypercholesterolemia, which is commonly known as high blood cholesterol level, can lead to many medical complications such as atherosclerosis. Atherosclerosis is one of the most significant forms of cardiovascular disease because of its frequent occurrence and its predilection for serious ailments such as coronary thrombosis. Atherosclerosis is characterized by the thickening of the intima, reduction in diameter, and loss of elasticity of arteries, due to fatty accumulations. Higher blood levels of cholesterol are observed in atherosclerosis patients than in normal persons. Accordingly, it is considered important in the treatment and prevention of atherosclerosis to maintain normal blood cholesterol levels.

The common therapy for treating hypercholesterolemia, when blood cholesterol levels are not excessively high, but higher than average, has been the consumption of a low fat diet, devoid as much as possible of animal fats. This necessitates reduced consumption of nutritious foods such as meat, milk and eggs. Although maintenance of a low fat diet can help control hypercholesterolemia in a large number of instances, for some individuals, additional means are required to lower the blood cholesterol level.

One of the major uses of cholesterol in the body is to serve as a precursor for bile acids. The bile acids, natural detergents, are secreted by the liver and enter the intestinal tract where they aid in the digestion and absorption of fats. The bile acids are then re-absorbed from the intestine and returned to the liver. The bile acids are secreted into the intestine again and the process repeats. Although the system operates very efficiently, a small percentage of bile acids escape recycle and are eliminated through the feces. The amount of bile acids lost is replenished by conversion of cholesterol to bile acids. The bile acid sequestrant resins interrupt the bile acid cycle by binding to the bile acids and thereby increasing the amount of bile acids excreted in the feces.

Bile acid sequestrant resins have been administered orally to reduce blood cholesterol levels. Well known resins include cholestyramine, a synthetic, strongly basic anion exchange resin containing quaternary ammonium functional groups which are attached to a styrene-divinylbenzene copolymer, and colestipol, N-(2-aminoethyl)-1,2-ethanediamine polymer with (chloromethyl)oxirane. The mechanism for lowering cholesterol by consumption of these sequestrants is well known.

Although the efficacy of bile acid sequestrant resins, and particularly cholestyramine, is well known, administration of the resin is unpleasant because the resin is not palatable and must be taken in relatively high doses of 4 to 24 grams per day. For most therapeutic treatment, the resin is generally suspended in a beverage such as water or in fruit juices and the beverage is consumed to supply cholestyramine to the intestinal system. Examples of such beverage resin suspensions are disclosed in U.S. Pat. Nos. 3,974,272; 4,172,120 and 4,064,234.

In addition to its unpalatable taste which is exacerbated by the requirement of high dosages of consumption of resin to enable efficacy, high levels of cholestyramine and other bile acid sequestrant resins can cause several side effects, such as constipation.

Thus, there exists a need in the art to treat hypercholesterolemia by utilizing a bile acid sequestrant resin containing composition wherein the composition exhibits a higher degree of in vivo efficacy.

Hoffman et al., "Sampling Intestinal Content with a Sequestering Capsule," Mayo Clin Proc, Mar 1976, Vol. 51 describes a non-invasive technique for sampling bile acid in man where a cholestyramine resin suspension is filled into a 1 cm dialysis tubing which is sealed with a surgical clip and placed in an opaque 00 gelatin capsule. The capsule is administered to humans as a means for studying bile acid metabolism. There is no suggestion in the paper of using the capsule to administer a bile acid sequesterant resin or using a dialysis tubing which selectively admits low molecular weight materials from the intestine.

SUMMARY OF THE INVENTION

The present invention provides an improved pharmaceutical composition comprising a bile acid sequestrant resin which is useful in treating hypercholesterolemia. In accordance with the invention, a bile acid sequestrant resin is maintained in a nondegradable membrane which permits bile acids from the digestive tract to pass through the membrane and bind to the sequestrant resin and prevents substances in the digestive tract having a higher molecular weight than bile acids from contacting and binding to the resin.

The present invention is based upon the discovery that when bile acid sequestrant resins are ingested as a powder, they are inactivated by high molecular weight anionic materials in the digestive tract. These high molecular weight materials bind to the sequestrant resin and occupy bonding sites which could otherwise be used to bond bile acids. It has been estimated that as little a 5% of the active sites of the sequestrant resin bind bile acids. By placing, coating, and/or encapsulating the sequestrant resin in a membrane which permits bile acids to pass through the membrane and contact the resin and excludes higher molecular weight materials, the efficiency with which the sequestrant resin binds bile acids is improved. As a consequence, it is anticipated that the sequestrant resin can be administered in lower dosages. Furthermore, because the resin is maintained within a membrane, the resulting composition is more palatable.

Bile acids range up to about 537 daltons in molecular weight. In accordance with one embodiment of the invention, a membrane is selected which excludes materials having a molecular weight greater than 2000 daltons. In a more preferred embodiment, a membrane is selected which excludes materials having a molecular weight greater than 1000 daltons and in a still more particularly preferred embodiment a membrane is selected which excludes materials having molecular weight greater than about 700 daltons. Those skilled in the art will appreciate that as the ability of the membrane to exclude materials having a molecular weight higher than that of bile acids improves, the efficiency with which the sequestrant resin binds bile acids improves and the dosage of the sequestrant resin can be reduced.

Accordingly, one embodiment of the present invention is a composition which comprises a bile acid sequestrant resin maintained in a nondegradable membrane wherein the membrane enables bile acids from the digestive tract to bind to the sequestrant resin while it prevents substances having a higher molecular weight than bile acids from contacting the resin. The membranes used in the present invention are preferably semipermeable resins although it is also believed that certain microporous materials may also be useful.

Another embodiment of the present invention relates to a method for lowering the blood cholesterol level in humans. The method comprises the step of orally administering a pharmaceutical composition comprising a bile acid sequestrant resin maintained in a nondegradable membrane, wherein said membrane enables bile acids from the digestive tract to contact and bind to said resin while preventing substances having a molecular weight greater than bile acids from contacting said resin. The composition is administered in a daily therapy which is designed to reduce cholesterol levels in the blood.

Accordingly, it is an object of the present invention to provide a pharmaceutical composition for treating hypercholesterolemia which utilizes a bile acid sequestrant resin having improved in vivo efficacy through the use of a membrane to exclude higher molecular weight materials and more particularly polyanions.

A further object of the present invention is to provide a pharmaceutical composition for treating hypercholesterolemia which can be administered in lower dosages and is more palatable.

These, and other objects will be readily apparent to those skilled in the art as reference is made to the following detailed description of the preferred embodiment.

DETAILED DESCRIPTION OF THE PREFERRED EMBODIMENT

In describing the preferred embodiment, certain terminology will be utilized for the sake of clarity. It is intended that such terminology include not only the recited embodiment, but all technical equivalents which operate in a similar manner, for a similar purpose, to achieve a similar result.

The present invention relates to a pharmaceutical composition useful for treating hypercholesterolemia comprising a bile acid sequestrant resin maintained in a semipermeable or microporous water-insoluble material; wherein said semipermeable or microporous material enables bile acids from the digestive tract to contact and bind to said resin while preventing substances having a molecular weight greater than bile acids from contacting said resin material.

The active material according to the present invention is a bile acid sequestrant resin. These resins, which are solid and typically granular in form, function to reduce the blood cholesterol level in humans using the above described mechanism. One resin which may be utilized as a bile acid sequestrant comprises a cholestyramine resin. The particle size of the resin typically ranges from about 100 to about 200 mesh. Cholestyramine is commercially available and sold by a number of drug manufacturers. An example of a commercially available cholestyramine resin is Questran, sold by Bristol Labs.

Another bile acid sequestrant resin which has been commonly employed is colestipol. This material is also commercially available and is sold in granular form by the Upjohn Chemical Company under the name Colestid. Cholestyramine is the bile acid sequestrant resin of choice.

The sequestrant resin is maintained in a nondegradable membrane which may be a semipermeable or microporous material. This material is particularly characterized by being capable of enabling bile acids from the digestive tract to contact and bind to the resin while preventing substances having a molecular weight greater than bile acids (e.g., greater than 2000 daltons, more preferably greater than 1000 daltons, and still more preferably, greater than 700 daltons) from contacting the resin. The pharmaceutical composition may be prepared by encasing each grain of resin in the semipermeable material, encasing a number of grains of the resin in the semipermeable material, or encasing a slurry including a number of grains dispersed in a solvent, such as water in the semipermeable material.

The term "nondegradable" as used herein means a material that is essentially resistant to digestion in the stomach and small intestine. Suitable membranes must be pharmaceutically acceptable for ingestion. They may be surface active in the sense that they swell in the gastrointestinal tract and admit the bile acids.

Examples of polymeric materials useful as semipermeable membranes in the present invention include polymeric substrates, such as those produced for dialysis tubing. One such semipermeable water-insoluble material is a benzoylated cellulose tubing, and more particularly, a benzoylated ethylcellulose material. Such a tubing is available from Sigma Chemical Company, St. Louis, Missouri, under the designation D2272. According to literature, this tubing is useful for separating compounds with a molecular weight of 1200 or less from compounds with a molecular weight over 2000. As would be readily understood by one skilled in the art, other sizes of dialysis tubing may be utilized, as long as the pore size of the tubing is such that materials having a molecular weight greater than 2000 daltons and most preferably greater than 550 to 600 daltons do not penetrate the membrane.

Polymers used in the art of size exclusion chromatography may also be useful in the present invention. One of these dextran polymers with desirable size exclusion characteristic was developed by Johnson and Johnson as a topical agent to promote wound healing and sold under the tradename, Debrisan. This material consists of beads of cross-linked dextran having a porosity large enough to allow substances with a molecular weight of less than 1000 to enter freely. Substances with a molecular weight of 1000-5000 enter the beads less freely, while those with a molecular weight greater than 5000 remain outside the beads.

Alternatively, the bile acid sequestrant resin may be maintained in materials such as those disclosed for use in the Alza semipermeable osmotic regulated drug delivery systems (Alza Corp., Palo Alto, California). Such membranes are disclosed in U.S. Pat. Nos. 3,845,770; 3,916,899; 4,256,108; and 4,519,801. One such material includes the combination of a cellulose ether with either a pharmaceutically acceptable water-soluble polymer or a pharmaceutically acceptable water-insoluble polymer.

A preferred cellulose ether is ethyl cellulose. Ethyl cellulose is a non-toxic polymer, insoluble in water, essentially insoluble in the digestive system, soluble in the organic solvent ethyl alcohol and in solvent systems consisting essentially of alcohol and water. A preferred ethyl cellulose has an ethoxy group degree of substitution of 1.5 to 3 about 40 to 50% ethoxy content; and a viscosity range of 7 to 100 centipoises, or higher. Alternatively, a cellulose acetate material may be substituted for the cellulose ether.

The membrane may also contain a wall forming pharmaceutically acceptable water insoluble polymer, or a pharmaceutically acceptable water soluble polymer or a pharmaceutically acceptable water soluble agent as a permeability enhancer. In selecting the permeability enhancer, it is important to note that permeability enhancers which bind to the bile acid sequestrant resin such as anionic compounds containing acid or carboxyl groups should not be used or they should be thoroughly removed by washing from the semipermeable membrane before the membrane is used to enclose the sequestrant resin composition. If the membrane formulation is directly coated on the sequestrant resin, permeability enhancers containing carboxyl or other acidic groups should be omitted from the membrane formulation in order to avoid partial or total inactivation of the anion exchange resin. These polymers or agents, in either embodiment, are permeability enhancers that aid in regulating the passage of fluid through the membrane.

Representative of water soluble polymers and agents can be selected subject to the aforementioned qualification as to anionic compounds from the group consisting essentially of water soluble polymers such as celluloses represented by hydroxypropyl cellulose, hydroxypropyl methylcellulose, hydroxyethyl cellulose, ethyl methylcellulose, methylcellulose, acrylics including polyacrylic acid, polyethyl methacrylate, polymethyl methacrylate, pyrrolidones including polyvinyl pyrrolidone, alkylated vinylpyrrolidone polymers, poly(vinylpyrrolidone/vinyl acetate)copolymers, vinylpyrrolidone/dimethylaminoethylmethacrylate copolymers, maleic acid polymers such as monobutyl ester of poly(methylvinylether/maleic acid), monoethyl ester of poly(methylvinylether/maleic acid), poly(methyl vinylether/maleic anhydride)copolymer, polyvinyl alcohol hydrolyzed 75 to 85%, water soluble agents such as polyethylene glycol, polyethylene oxide, guar gum, gum arabic, dextran, citric acid, triethyl citrate, acetyltriethyl citrate, sucrose, fructose, glycerin, triacetin, and the like.

Representative of water insoluble, alcohol-water soluble or dispersable polymers may be selected from the group consisting essentially of carboxy polymers, blended with hydroxy polymers and insolubilized by curing with an energy source. One such example is carboxyvinyl polymer, also known as carboxypolymethylene, a polymer consisting of acrylic acid crosslinked with polyallyl sucrose as described in U.S. Pat. Nos. 2,798,053 and 2,909,462 as sold under the trademark Carbopol. A preferred hydroxy polymer is hydroxypropyl cellulose sold under the trademark Klucel. A preferred ratio of these is polyhydroxy:polycarboxy 4:1. Other carboxy polymers can optionally be used including poly(methyl vinylether maleic anhydride), ethylene/acrylic acid copolymer, ethylene maleic acid anhydride copolymers, methacrylic acid ethylacrylate copolymers, and the like. Other hydroxy polymers include hydroxyethyl cellulose, hydroxyethyl starch, poly(hydroxyethyl methacrylate), hydroxybutyl methylcellulose, and the like. Other representative water-insoluble, alcohol-water soluble polymers include cellulose nitrate, polyalkyds, polyvinyl acetal, polyvinyl butyral, vinyl alcohol-vinyl acetate copolymer, vinyl alcohol-vinyl butyral copolymer, polyethylacrylate and the like.

Optionally, water insoluble agents can be included as plasticizers in the wall to increase its flexibility. Agents in this group include tributyl citrate, acetyltributyl citrate, acetyl-tri-2-ethylhexayl citrate, tributyl sebeccate, castor oil, mono-, di- and triglycerides, and oils such as corn, cottonseed, peanut and soya.

Before extraction of any acidic or carboxyl containing components, the amount of the (a) primary wall forming cellulose ether present in the wall is about 20 to 90 wt%, the amount of (b) any water soluble hydrophilic polymer or hydrophilic agent is about 10 to 50 wt%, the amount of (c) any water insoluble, hydrophilic polymer is about 10 to 80 wt%, or, (d) the composite wall consists of (a) and a mixture of (b) and (c), with the semipermeable composite wall comprising 100 wt%.

The membrane may take the form of a microporous material, as long as the pores of the material are small enough to block passage of materials having molecular weight greater than 2000 daltons through the material. On the other hand, the size of the pores must be large enough to enable the bile acids maintained in the digestive tract to pass through the pores and contact the sequestrant resin. In practice, materials having a pore size ranging from about 20 to 100 Angstroms are suited for use in the present invention.

Microporous materials having a preformed structure are commercially available and they can be made by art-known methods. The microporous materials can be made by etched nuclear tracking, by cooling a solution of flowable polymer below the freezing point whereby solvent evaporates from the solution in the form of crystals dispersed in the polymer and then curing the polymer followed by removing the solvent crystals, by stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes*, by R.E. Kesting, Chapters 4 and 5, 1971, published by McGraw Hill, Inc.; *Chemical Reviews*, Ultrafiltration, Vol. 18, pages 373 to 455, 1934; *Polyiner Eng. and Sci.*, Vol 11, No. 4, pages 284 to 288, 1971; *J. Appl. Poly. Sci.*, Vol. 15, pages 811 to 829, 1971; and in U.S. Patent Nos. 3,565,259; 3,615,024; 3,751,536; 3,801,692; 3,852,224; and 3,849,528.

Microporous materials include microporous polycarbonates comprised of linear polyesters of carbonic acid in which carbonate groups recur in the polymer chain, microporous materials prepared by the phosgenation of a dihydroxyl aromatic such as bisphenol A, microporous poly(vinylchloride), microporous polyamides such as polyhexamethylene adipamide, polycaprolactam, polyamides derived from p-amino benzoic acid, paraphenylene diamine and terephthalic acid derivatives, microporous modacrylic copolymers including those formed from poly(vinylchloride) 60% and acrylonitrite, porous polysulfones characterized by diphenylene sulfone groups in a linear chain thereof, halogenated poly(vinylidene), polychloroethers, acetal polymers, polyesters prepared by esterification of a dicarboxylic acid or anhydride with an alkylene polyol, polyesters prepared by esterification of hydroxy carboxylic acids or esters, polyesters formed by ring opening polycondensation of cyclic lactones, poly(alkylenesulfides), phenolic polyesters, microporous poly(saccharides), microporous poly(saccharides) having substituted and unsubstituted anhydroglucose units, asymmetric porous polymers, crosslinked olefin polymers, hydrophobic or hydrophilic microporous homopolymers, copolymers or interpolymers having a reduced bulk density, and materials described in U.S. Pat. Nos. 3,597,752; 3,643,178; 3,654,066; 3,709,774;, 3,718,532; 3,803,061; 3,852,224; 3,853,601; and 3,852.388, Canadian Patent 1,239,034 in British Patent No. 1,126,849, EP 273,069 and in *Chem. Abst.*, Vol 71 4274F, 22572F, 22573F, 1969.

Additional microporous materials include poly(urethanes), cross-linked, chain-extended poly(urethanes), microporous poly(urethanes) in U.S. Pat. No. 3,524,753, poly(imides), poly(benzimidazoles), collodion (cellulose nitrate with 11% nitrogen), regenerated proteins, crosslinked gelatin semi-solid cross-linked poly(vinylpyrrolidone), the microporous materials disclosed in U.S. Pat. No. 3,615,024 and U.S. Pat. Nos. 3,646,178 and 3,852,224.

Further, the microporous forming material used for the purpose of the invention, includes the embodiment wherein the microporous material is formed in situ, by a pore-former being removed by dissolving or leaching it to form the microporous material during the operation of the system. The pore-former can be a solid or a liquid. The term liquid, for this invention embraces semi-solids, and viscous fluids. The pore-formers can be inorganic or organic. The pore-formers suitable for the invention include pore-formers that can be extracted without any chemical change in the polymer.

In some embodiments, it may be desirable to utilize both a microporous inner membrane surrounding the active material, and a semipermeable membrane surrounding the microporous material. Materials containing both a microporous and a semipermeable membrane are disclosed in U.S. Pat. No. 4,256,108.

To form the pharmaceutical composition, the semipermeable or microporous material is formed around granules, pellets, or a slurry of the bile acid sequestrant resin. The semipermeable or microporous material can be applied by molding, fluidized bed, spraying, dipping, or pan coating around the granules. In another embodiment, the wall material can be cast into a film shaped to desired dimensions, sealed to define a hollow compartment that is filled with the granules, and then closed. The composition may also be manufactured in the form of a hollow fiber which is loaded with the resin material as it is formed or subsequent to forming. The hollow fiber may be cut and sealed to desired lengths.

The membrane may also be manufactured with an empty compartment comprising the wall material, that is filled with the resin material. For example, when utilizing commercially available dialysis membranes as the starting material, one end of the dialysis membrane may be sealed, the bile acid sequestrant resin or slurry may be filled into the open end of the dialysis membrane, and the opposite end of the dialysis membrane can be sealed. High frequency electronic techniques may also be used. Another preferred technique that can be used is the air suspension procedure. This procedure consists of suspending and tumbling the resin, and, other ingredients, in a current of air and the wall forming compositions until the wall is applied to the agent. This procedure is described in U.S. Pat. No. 2,799,241. The encapsulated or encased sequestrant resin may be administered in the form of a tablet or capsule.

Once the composition including the resin and osmotic solute, if present, maintained in the membrane has been produced, it is then available for patient use. However, it may be desirable to insert the pharmaceutical composition into another material to facilitate swallowing. For example, the resin/membrane composition may be inserted into a capsular material, such as gelatin capsules which are commonly used in the pharmaceutical industry. Moreover, the size of the capsule should be small enough to enable easy swallowing. For example, capsules having a length of approximately 1 cm may be utilized. The amount of resin maintained inside both the capsule outer wall and the membrane material can range from about 0.05 grams to about 1.0 grams. A particularly preferred dosage comprises 0.5 grams of resin per capsule. Maintenance of the resin in a capsule provides a convenient way for the patient to take the drug. Alternatively, the resin may be added to food or drink.

To reduce hypercholesterolemia, a patient simply ingests the pharmaceutical composition, preferably maintained inside a gelatin capsule to improve palatability and to enable ease of swallowing in a daily therapy which is capable of producing a sustained reduction in his or her cholesterol level. Once in the digestive tract, fluid present in the digestive tract functions to dissolve the outer gelatin capsule walls to thereby expose the resin/membrane to the digestive tract. Once exposed, the bile acids present in the digestive tract can diffuse through the membrane to thereby bind to the sequestrant. As has been discussed above, this enables the reduction of cholesterol in the blood stream by requiring the cholesterol present to regenerate bile acids.

Depending on the amount of resin maintained in each capsule, and the amount of cholesterol reduction which is desired, 1 to 12 grams of resin is administered daily. This can lead to a 30 to 75% reduction in the amount of resin consumed daily as compared to amounts which are typically consumed by dispersion in a beverage.

A critical feature of the present invention is that the membrane be able to prevent materials having a molecular weight greater than bile acids from diffusing through the semipermeable material. Laboratory studies have demonstrated that the use of sequestrant resins, such as cholestyramine, are very inefficient when used in vivo. For example if one compares the amount of bile acids which cholestyramine can bind in vitro under ideal conditions to that which it binds in vivo, its efficiency is less than 10%. One of the causes of the in vivo inefficiency is believed to be that the cholestyramine resin is fully exposed to the digestive system. As a result, high molecular weight anionic materials, endogenous to the digestive tract or introduced in the diet (e.g., pigments, bilirubin, urobilins, anionic complexes from incomplete digestion of dietary fibers or the like), tend to bind to the resin. The binding of these materials to the resin reduces the amount of binding sites available for the bile acids. Accordingly, the binding efficiency is significantly reduced. By maintaining the cholestyramine resin in a membrane in accordance with the present invention, the high molecular weight substances do not bind to the resin, thereby rendering more of the resin capable of binding to the bile acids. Once the bile acids have bound to the resin, they remain tightly bonded, and are excreted, along with the semipermeable material, through the feces.

The present invention is illustrated in greater detail by the following examples.

EXAMPLE

For use as a standard, 2 cm lengths of dialysis tubings with a pore sizes corresponding to molecular weights of 1,000, 2,000 and 50,000 daltons was cut. One end of the tubing was ligated with nylon thread to form a seal. Into the open end of the tube was inserted 100 mg cholestyramine resin in one ml of water. The open end of the tubing was then sealed by ligation with nylon thread and this process was repeated to produce five samples. Five dogs, each receiving a conventional dry dog food diet, orally ingested each of the three bags containing the cholestyramine resin. The bags were collected from the dogs through the feces and the contents of the bags were removed and assayed for total bile acid content. The amount of bile acid recovered was expressed as the percentage of the resin sites bound. The results are shown in the Table.

TABLE

EFFICIENCY OF BILE ACID BINDING BY CHOLESTYRAMINE ENCASED IN DIALYSIS BAGS HAVING DIFFERENT PORE SIZES.

Percentage of Total Sites Bound

| Dog # | 50,000 (Ref) | 2000 | % Increase Over Ref. | 1000 | % Increase Over Ref. |
|---|---|---|---|---|---|
| 1 | 3.52 | 6.64 | 88.6 | 4.88 | 38.6 |
| 2 | 1.69 | 3.84 | 127 | 3.13 | 85.2 |
| 3 | 3.06 | 3.52 | 15 | 4.04 | 32 |
| 4 | 2.93 | N.D.* | — | 4.82 | 64.5 |
| 5 | 1.30 | 2.67 | 105 | 2.54 | 95.4 |
| Avg. | 2.50% | 4.17% | 66.8 | 3.88% | 55.2 |

*Sample was broken when recovered

The results as shown in the Table demonstrate that encasing the cholestyramine in a semipermeable material having a pore size equal to or less than 2000 daltons increases bile acid binding potency in individual cases by over 100% compared to the 50,000 dalton pore size standard, with the increase for all examples averaging 55-67%. Accordingly, due to its improved efficacy, lesser amounts of resin material should be required to lower hypercholesterolemia, and the side effects associated with sequestrant resin consumption can be minimized. This provides a superior alternative to presently available methods of treatment using bile acid sequestrant agents.

Having described the invention in detail and by reference to specific embodiments thereof, it will be apparent that numerous modifications and variations are possible without departing from the spirit and scope of the invention as defined by the following claims.

What is claimed is:

1. A pharmaceutical composition useful for treating hypercholesterolemia comprising a solid granular bile acid sequestrant resin enclosed in a semipermeable or microporous membrane wherein said membrane enables bile acids from the digestive tract to contact and bind to said resin while preventing substances having a molecular weight greater than 2000 daltons from contacting and binding to said resin.

2. The composition according to claim 1 wherein said bile acid sequestrant resin is selected from the group consisting of cholestyramine and colestipol.

3. The composition according to claim 2 wherein said bile acid sequestrant resin is cholestyramine.

4. The composition according to claim 3 wherein said membrane is a semipermeable membrane.

5. The composition of claim 4 wherein said membrane prevents materials having a molecular weight greater than 1000 daltons from contacting said resin.

6. The composition of claim 5 wherein said membrane prevents materials having a molecular weight greater than 700 daltons from contacting said resin.

7. The composition according to claim 4 wherein said semipermeable membrane comprises cellulose acetate, cellulose ether, a combination of cellulose ether and a pharmaceutically acceptable water-insoluble polymer, or a combination of a cellulose ether and a pharmaceutically acceptable water soluble polymer.

8. The composition according to claim 7 wherein said semipermeable membrane comprises a combination of ethylcellulose and a pharmaceutically acceptable water insoluble polymer.

9. The composition according to claim 7 wherein said semipermeable membrane comprises a combination of ethylcellulose and a pharmaceutically acceptable water soluble polymer.

10. The composition according to claim 3 wherein said membrane is a microporous material wherein the size of the pores of said microporous material ranges from about 20 to 100 angstroms.

11. A method for lowering the blood cholesterol level in humans comprising the step of:
orally administering a pharmaceutical composition comprising a solid granular bile acid sequestrant resin enclosed in a semipermeable or microporous membrane, wherein said membrane permits bile acids from the digestive tract to contact and bind to said resin while preventing substances having a molecular weight greater than 2000 daltons from contacting said resin, said composition being administered in a therapy which is capable of reducing cholesterol levels in the blood.

12. The method according to claim 11 wherein said bile acid sequestrant resin is selected from the group consisting of cholestyramine and colestipol.

13. The method according to claim 12 wherein said bile acid sequestrant is cholestyramine.

14. The method according to claim 13 wherein said membrane is a semipermeable membrane.

15. The method of claim 14 said semipermeable membrane excludes materials having a molecular weight greater than 1000 daltons from contacting said resin.

16. The method of claim 15 wherein said semipermeable membrane excludes materials having a molecular weight greater than 700 daltons from contacting said resin.

17. The method according to claim 14 wherein said semipermeable membrane comprises cellulose acetate, cellulose ether, a combination of cellulose ether and a pharmaceutically acceptable water-soluble polymer or a combination of cellulose ether and a pharmaceutically acceptable water insoluble polymer.

18. The method according to claim 17 wherein said semipermeable membrane comprises a combination of ethylcellulose and a pharmaceutically acceptable water-insoluble polymer.

19. The method according to claim 17 wherein said semipermeable membrane comprises a combination of ethylcellulose and a pharmaceutically acceptable water soluble polymer.

20. The method according to claim 13 wherein said membrane is a microporous material wherein the size of the pores of said microporous material ranges from about 20 to about 100 Angstroms.

21. The method according to claim 14 wherein said composition is maintained in an outer gelatin capsule.

22. The method according to claim 21 wherein the amount of cholestyramine present in said capsule ranges from about 0.05 grams to about 1 gram.

23. The method according to claim 11 wherein the amount of resin administered ranges from about 1 gram to about 10 grams daily.

24. The composition of claim 1 wherein said solid granular resin has a particle size of about 100 to 200 mesh.

25. The method of claim 11 wherein said solid granular resin has a particle size of about 100 to 200 mesh.

* * * * *